(12) United States Patent
Desinger et al.

(10) Patent No.: US 8,452,422 B2
(45) Date of Patent: May 28, 2013

(54) FLEXIBLE APPLICATION DEVICE FOR THE HIGH-FREQUENCY TREATMENT OF BIOLOGICAL TISSUE

(75) Inventors: Kai Desinger, Berlin (DE); Thomas Stein, Berlin (DE); André Roggan, Berlin (DE); Markus Fay, Teltow (DE)

(73) Assignee: Celon AG (DE)

( * ) Notice: Subject to any disclaimer, the term of this patent is extended or adjusted under 35 U.S.C. 154(b) by 586 days.

(21) Appl. No.: 11/920,400

(22) PCT Filed: Apr. 21, 2006

(86) PCT No.: PCT/EP2006/061762
§ 371 (c)(1),
(2), (4) Date: Jan. 23, 2009

(87) PCT Pub. No.: WO2006/120116
PCT Pub. Date: Nov. 16, 2006

(65) Prior Publication Data
US 2009/0204060 A1 Aug. 13, 2009

(30) Foreign Application Priority Data

May 13, 2005 (DE) .......................... 10 2005 023 303

(51) Int. Cl.
*A61N 1/02* (2006.01)
(52) U.S. Cl.
USPC ........................................................ 607/154
(58) Field of Classification Search
USPC ..... 607/96, 98, 104, 153, 133, 124, 115–116;
606/27–31; 600/98, 154, 124, 133, 96, 115–116,
600/109
See application file for complete search history.

(56) References Cited

U.S. PATENT DOCUMENTS 5,807,395 A * 9/1998 Mulier et al. .................. 606/41
6,014,589 A 1/2000 Farley et al.
(Continued)

FOREIGN PATENT DOCUMENTS

DE 44 42 690 6/1996
DE 101 28 701 5/2003
(Continued)

OTHER PUBLICATIONS

International Search Report, Jun. 29, 2000.

*Primary Examiner* — Carl H Layno
*Assistant Examiner* — Paula J Stice
(74) *Attorney, Agent, or Firm* — Ostrolenk Faber LLP (57) ABSTRACT

The invention concerns a flexible application device (1) for the high-frequency therapy of biological tissue or hollow organs, including a tubular high-frequency catheter (5) with a flexible shaft tube (6) having at least one lumen passing therethrough, a head electrode (2) arranged at the distal end of the high-frequency catheter (5), an electric line (9) with a connection (20) for a high-frequency generator (11), and a connecting element (8) arranged at the proximal end of the shaft tube (6) between the shaft tube and the line (9). An electrically conducting traction element (12) extends in the lumen between the head electrode (2) and the connecting element (8) and is fixedly connected to the head electrode (2) on the one hand and the connecting element (8) on the other hand in such a way and which is of such a tensile strength that all external forces which occur during a treatment and which act on the high-frequency catheter (5) can be transmitted to the connecting element (8) by way of the head electrode (2) and the traction element (12).

33 Claims, 3 Drawing Sheets

| U.S. PATENT DOCUMENTS | | | |
|---|---|---|---|
| 6,036,687 A | 3/2000 | Laufer et al. | |
| 6,071,277 A | 6/2000 | Farley et al. | |
| 6,514,251 B1 | 2/2003 | Ni et al. | |
| 6,905,510 B2 * | 6/2005 | Saab | 607/105 |
| 2003/0088242 A1 | 5/2003 | Prakash et al. | |
| 2004/0162555 A1 | 8/2004 | Farley et al. | |
| 2004/0167517 A1 | 8/2004 | Desinger et al. | |

| FOREIGN PATENT DOCUMENTS | | |
|---|---|---|
| EP | 0714635 | 6/2002 |
| JP | 11-262530 | 9/1999 |
| JP | 2004-527359 | 9/2004 |
| WO | WO 00/36985 | 6/2000 |

* cited by examiner

FLEXIBLE APPLICATION DEVICE FOR THE HIGH-FREQUENCY TREATMENT OF BIOLOGICAL TISSUE

CROSS-REFERENCE TO RELATED APPLICATIONS

This application is a national stage filing of and claims priority to PCT/EP2006/061762, filed Apr. 21, 2006 and claims priority to German Patent Application 10 2005 023 303.1 dated May 13, 2005.

BACKGROUND OF THE INVENTION

The invention concerns a flexible application device for the high-frequency therapy of biological tissue. The application device includes a tubular high-frequency catheter with a preferably flexible shaft tube which has at least one lumen therethrough and which fits to or in a connecting element, and at least one head electrode arranged at the distal end of the high-frequency catheter.

In particular the invention concerns an application device for endoluminal or interstitial-endoscopic use.

Application devices for high-frequency therapy are known. During such a therapy procedure applying a high-frequency ac voltage between two electrodes provides for a thermal in-depth heating effect in respect of the tissue surrounding the electrodes. The so-called active regions of the electrodes are in electrically conductive relationship with the body tissue after being introduced into the body of the patient. The ohmic tissue resistance which is a part of the complex tissue impedance provides for conversion of the alternating current applied by way of the electrodes into Joule heat. At temperatures of between 50° C. and 100° C., denaturing of the body-specific proteins occurs (coagulation) and consequently the affected areas of tissue shrink or die off. By virtue of the high current density at the active electrodes the heating effect occurs predominantly in the region of those electrodes so that local thermal application is possible.

U.S. Pat. No. 6,014,589, U.S. Pat. No. 6,036,687, U.S. Pat. No. 6,071,277 and US 2004/0162555 A1 disclose methods and various devices for the high-frequency therapy of hollow organs, in particular for the treatment of veins.

Application devices for the high-frequency therapy of or in hollow organs of the general kind set forth include a tubular high-frequency catheter with a flexible shaft tube having at least one lumen passing therethrough, a head electrode arranged at the distal end of the high-frequency catheter, an electric line with a connection for a high-frequency generator, and a connecting element between the shaft tube and the line.

SUMMARY OF THE INVENTION

Now the object of the present invention is to provide an application device of the general kind set forth, which affords a greater degree of certainty and safety in use.

In accordance with the invention that object is attained by a flexible application device for the high-frequency therapy of biological tissue, which has a traction element which extends between the head electrode and the connecting element and which is fixedly connected to the head electrode on the one hand and the connecting element on the other hand in such a way and the cross-sectional area of which and the tensile strength of which are such that all external forces which occur during a treatment and which act on the high-frequency catheter can be transmitted into the connecting element by way of the head electrode and the traction element.

The invention is based on the realisation that, in the case of conventional application devices, the external forces which occur during a treatment and which act on the high-frequency catheter are substantially transmitted to the connecting element by way of external components of the application device. The external component of the application device which usually include a fluid-tight, electrically insulating casing are frequently made up of a plurality of pieces in the longitudinal direction of the high-frequency catheter so that there are a plurality of connecting locations by way of which the external forces have to be transmitted, as considered in the longitudinal direction of the high-frequency catheter. Each of the connecting locations however represents a potential weak point. That gives rise to the risk of individual components of the high-frequency catheter coming loose or even entirely tearing away, under a mechanical loading. That problem is effectively obviated by a traction element which extends continuously from the head electrode to the connecting element and which is suitably fixedly secured to the head electrode on the one hand and the connecting element on the other hand.

The shaft tube of the high-frequency catheter preferably forms an electrically insulating casing which encloses the lumen or is provided with such a casing.

In a preferred variant the head electrode is electrically connected to an electrical contact location in the connecting element by way of an electrically conducting feed line which extends within the electrically insulating casing. In a particularly preferred fashion that feed line forms the traction element itself and thus involves a dual function of electrical conductor and securing element. With a suitable choice in respect of the feed line material and with suitable dimensioning the mechanical demands on the traction element and the electrical demands on the feed line can be equally fulfilled.

The feed line as the traction element is preferably of a tensile strength of at least 1000 N/mm$^2$ and of a diameter of between 0.2 and 0.8 mm, particularly preferably being 0.4 mm. With a diameter of 0.4 mm a traction element of that kind can transmit tensile forces of more than 125 N from the head electrode to the connecting element. That tensile force is sufficient to transmit all external forces from the head electrode to the connecting element, in the event of failure of all connecting locations between the casing of the shaft tube and the electrodes as well as between the potentially several electrodes and the respective insulator elements. In that case the traction element functions as a safety element. The external forces acting on the high-frequency catheter upon being pulled out of the tissue are usually directed in the longitudinal direction of the high-frequency catheter. The head electrode carries those forces and passes them by way of the traction element in the form of tensile forces to the connecting element. In the event of failure of all connecting locations of the external components of the high-frequency catheter, those external components are still pulled like a string of beads on to the feed line serving as the traction element and in that way are connected together by the feed line. The external components of the high-frequency catheter are prevented from slipping off by the head electrode being of a diameter which prevents that.

Particularly preferably the tensile strength of the traction element and the connection to the head electrode is in the range of between 70 and 300 N.

The details relating to the tensile strength refer in the context of this description to the maximum value of the tensile stress for a respective material, which arises as a maximum value $R_m$ out of a stress-strain curve which is ascertained in a tensile test. The tensile strength is calculated from the quotient of a maximum tensile force and the initial cross-section of the sample (unit of measurement: $N/mm^2$).

The above-mentioned preferred diameter of the feed line of the head electrode in the range of between 0.2 and 0.8 mm, besides an adequate maximum tensile force and good electrical conductivity, also permits easy integration of the high-frequency catheter into existing application devices. Furthermore lines of that diameter guarantee a level of flexibility which is adequate for endoluminal or interstitial-endoscopic application.

A particularly suitable material for the feed line as a traction element is a rust-resistant metal such as titanium or stainless steel. Those metals enjoy a suitably high level of tensile strength and at the same time, by virtue of the dimensioning of the diameter of the feed line, also afford adequate electrically conductivity.

In a particularly preferred variant the feed line of the head electrode consists entirely or in parts of stainless steel which is also referred to as V2A steel. The material has a high tensile strength and is biocompatible. In an alternative embodiment the feed line can be a braided wire comprising a large number of individual filaments of stainless steel. That also ensures the flexibility of the high-frequency catheter, which is necessary for the application—particularly with the above-mentioned preferred diameters for the feed line. The choice of the material steel is particularly preferred whenever the head electrode also consists of steel at least in a connecting region of the feed line. In that case a homogeneous and high-strength connection can be formed by welding between the feed line and the head electrode, which also withstands high mechanical loadings.

The coagulation volume of application devices is limited by the tissue drying out after a certain application time due to evaporation of the tissue fluid in the proximity of the electrodes where temperatures of over 100° C. occur. That drying-out effect causes a rise in the specific resistance of the tissue. If at least one electrode is completely enclosed by dried-out tissue, that involves a rapid rise in the terminal impedance so that further input of energy into the tissue is prevented. That is equivalent to the application being broken off, even if the high-frequency generator remains switched on.

Internal flushing of the high-frequency catheter with a temperature-controlled medium (for example water) means that this procedure can be avoided within certain limits. By means of an internal fluid circuit the electrodes are permanently kept at the temperature of the fluid flowing through the arrangement. When choosing a fluid temperature which is ambient temperature, it is already possible to prevent the tissue from heating up in the proximity of the electrodes to such a degree that the tissue dries out. The regions at the highest temperature which in the case of a non-flushed high-frequency catheter are directly at the electrode surface are displaced into deeper layers of the tissue. The tissue in the proximity of the electrodes retains its water and electrolyte content and thus does not lose in terms of electrical conductivity. The consequence of this is that, even after long application times and at high power levels, electrical energy can be transformed into heat there.

Electrode temperature control is based on a counterflow fluid circuit. In a preferred variant the traction element is in the form of a tube in which the fluid is passed to the tip of the high-frequency catheter and flows back along the electrodes to the proximal end of the high-frequency catheter. The amount of fluid which is pumped through the high-frequency catheter is between 10 and 100 ml per minute.

A further possible way of preventing the electric current from breaking down due to a rise in impedance as a consequence of tissue dehydration is open flushing. With that principle, preferably electrically conducting fluid (for example physiological saline solution) is pumped through small bores or slots at the distal end of the high-frequency catheter (for example in the electrodes or in the insulator which in a bipolar arrangement is between the electrodes), into the tissue. In that situation, preferably only very small amounts of fluid are discharged into the tissue and at best only when dehydration begins or is present. For that purpose control of the pump can be effected in impedance-dependent fashion: when a rise in impedance is detected, which is to be equated to tissue dehydration in the proximity of the electrodes, then the pump delivers fluid until the impedance is restored to a normal value. The amounts of fluid which are delivered here in a pump procedure are a multiple less than in the above-described closed fluid circuit and are for example between 10 and 200 ml per hour. The increase which can be achieved in the electrical conductivity of the tissue can be adapted to the needs involved not just by a variation in the flushing amount but also the salt concentration of the solution.

Still other kinds of fluids can be used for the open flushing principle.

Therapeutically Effective Fluid:

A therapeutically effective medicament can be injected directly into the treatment location through small bores or slots at the distal end of the high-frequency catheter. It is possible to envisage here for example a chemotherapy medicament which particularly well destroys the tumor cells which are heated by means of high-frequency current or which leads to thermal sensitisation of the tumor cells and thus increases the effectiveness of the thermotherapy. It is however also possible to inject a local anaesthetic into the tissue to be treated in order to reduce the pain which occurs due to the increase in temperature of the tissue after the high-frequency current is switched on.

Toxic Fluid:

It is known that local destruction of tumor cells can be implemented by the injection of highly concentrated alcohol. In the case of the invention the injection can be effected through small bores or slots at the distal end of the high-frequency catheter and supplement the thermotherapy effect. The delivery of a toxic substance (such as for example high-percentage alcohol or a highly concentrated salt solution) can also be effected after the thermotherapy while the high-frequency catheter is being pulled out of the tissue in order to avoid spreading tumor cells.

Mixture:

Finally a mixture of electrically conducting, therapeutically effective and toxic fluids which can be adapted to the respective treatment and optimised is also possible.

Preferably the application device is in the form of a bipolar application device with a second proximal electrode which is electrically insulated with respect to the head electrode. The proximal electrode is arranged in the proximity of the distal end of the high-frequency catheter and electrically conductingly connected by way of a second electrical feed line to a second contact location in the connecting element. The spacing between the head electrode and the proximal electrode is preferably between 5 and 20% of the electrode length (with a bipolar configuration that corresponds to the overall length of distal and proximal electrodes). That spacing has proven to be particularly suitable for tissue sclerosis by means of a high-frequency alternating current.

The diameter of the high-frequency catheter, in particular the outside diameter of the shaft tube and the outside diameter of the proximal electrode and the largest diameter of the head electrode are preferably approximately equal to each other. In that respect the head electrode is preferably of its largest diameter at the proximal end of its outwardly directed peripheral wall. The head electrode is for example of a hemispherical shape towards its distal end. As an alternative thereto it can have a trocar ground configuration or can be pointed in a conical or wedge-shaped configuration.

The largest diameter of the head electrode and the diameter of the proximal electrode and of the rest of the high-frequency catheter is preferably less than 3.5 mm.

In regard to preferred uses the length of the shaft tube is between 300 and 3000 mm. The traction element passing therethrough is also to be of a corresponding length.

An application device of that kind is suitable for known uses and in addition embraces new therapy methods and areas of application.

Endoluminal Use of the Device:

For endoluminal use the high-frequency catheter of the application device is introduced into the lumen of a hollow organ, in particular a vessel. A high-frequency ac voltage is then applied to the electrodes. The position of the electrodes in the hollow organ can be altered by pushing it forward and pulling it back or by reciprocating it or by a rotary movement about its own axis.

For endoluminal use the head electrode is rounded and is shorter in terms of its longitudinal extent than the proximal electrode. The diameter of the high-frequency catheter of an application device for endoluminal use is to be adapted to the diameter of the hollow organ or vessel to be treated. In an endoluminal use the hollow organ to be treated, in particular the vessel wall, has current flowing therethrough, it heats up and coagulates. The hollow organ or the vessel consequently reduces its inside diameter or is completely closed.

Operating Procedure Using the Example of Varicose Veins:

A blood vessel to be treated, preferably the Vena saphena magna, is firstly preferably opened in the proximity of the ankle. The high-frequency catheter is then introduced with its distal end leading into the opened vein and advanced to the end of the vein. In the case of the Vena saphena magna that is the transition to the Vena formoralis. Optionally the Vena saphena magna can also be separated from the Vena formoralis (crossectomy) and the electrode advanced until it becomes visible at that opening. In that case, no high-frequency ac voltage leading to coagulation is yet applied to the electrode or electrodes of the high-frequency catheter. If no crossectomy is performed the position of the electrode head at the saphenofemoral transition is preferably monitored with sonographic imaging.

After the distal end of the high-frequency catheter with the head electrode is correctly positioned, a high-frequency ac voltage can be applied to the electrode provided for the treatment, and that voltage causes coagulation. In a monopolar arrangement the electrode intended for the treatment is the head electrode at the distal end of the high-frequency catheter. A counterpart electrode is previously applied to the body of the patient, as a neutral electrode of large area. If in accordance with a preferred variant a bipolar high-frequency catheter is used the high-frequency ac voltage is applied between the head electrode and the associated proximal ring electrode.

In order to contract the blood vessel over the desired length by coagulation the high-frequency catheter is then retracted slowly in the proximal direction. In that case the working speed is adapted to the geometry of the blood vessel to be treated and to the applied high-frequency ac voltage.

To increase the therapy effect, before the high-frequency ac voltage is applied, the blood which is in the vein can be pressed out with a cuff over the entire length of the vein.

In order to be able to approximately estimate the position of the electrode head at the distal end of the high-frequency catheter during the coagulation procedure (return movement), it is advantageous if a cord is tensioned in parallel relationship with the high-frequency catheter from the connecting element of the application device, in such a way that the end of the cord or a marked location on the cord outside the body of the patient is approximately level with the head electrode within the patient. In that fashion the high-frequency catheter can be retracted in the proximal direction particularly sensitively and at a uniform speed. Further possible options in regard to positional monitoring are sonographic imaging and palpation.

As soon as the head electrode leaves the portion to be treated of a blood vessel, the electrodes are separated form the high-frequency ac voltage again and the high-frequency catheter can be entirely withdrawn from the body of the patient.

If the application device is connected to a suitable control unit, the high-frequency ac voltage can be adapted to the respective demands involved, during coagulation. If the control unit is such that it outputs for example an acoustic or optical signal dependent on the impedance between the head electrode and the counterpart electrode, both the speed of withdrawal of the high-frequency catheter and also the magnitude of the high-frequency ac voltage can be particularly easily adapted to the respective requirements.

Operating Procedure Using the Example of the Fallopian Tube:

A further area of use of an application device with endoluminal involvement lies in the constriction or sclerosing of a Fallopian tube for sterilisation purposes. The electrode is introduced from the uterus into the Fallopian tube to be closed by means of a hysteroscope (endoscope for gynecology). The further procedure is the same as that of constricting veins (see above): after correct positioning of the electrode within the Fallopian tube high-frequency current is delivered and the electrode is retracted by a given distance so that the coagulated region contracts in respect of diameter and is thereby closed.

Interstitial-Endoscopic Use:

For interstitial-endoscopic use the high-frequency catheter of the application device is introduced into a working passage of an endoscope and advanced as far as the treatment location in order there to penetrate into the tissue to be treated and to destroy the tissue when an ac voltage is applied, as a consequence of coagulation. The use can be implemented for example with sonographic monitoring.

For interstitial-endoscopic use the head electrode preferably involves a conical or trocar grind. In addition preferably the electrode surface is at least region-wise of such a nature that the reflection of ultrasound is enhanced in order to facilitate sonographic monitoring of the application. Finally the application device, in an interstitial-endoscopic use, preferably has a guide tube or guide system. For interstitial-endoscopic use the diameter of the high-frequency catheter must be matched to the diameter of the working passage of the endoscope.

Treatment Procedure Using the Example of Pancreatic Tumors:

An area of use of an application device with interstitial-endoscopic involvement is the treatment of pancreatic tumors (pancreatic carcinomas). For that purpose the tubular high-frequency catheter of the application device is introduced into the stomach by way of a working passage of a gastroscope (endoscope for the gastrointestinal area) and fitted to the stomach wall over the pancreas. The pancreatic tumor is punctured with sonographic monitoring (endoscopic ultrasound) and the tumor tissue destroyed by coagulation.

Treatment Procedure Using the Example of Bronchial Tumors:

A further area of use of an application device with interstitial-endoscopic involvement is the treatment of bronchial tumors. For that purpose the high-frequency catheter is introduced into the bronchus in question through a bronchoscope (endoscope for the bronchial region) and placed with the distal end in front of the tumor. The tumor—which for example can obstruct the bronchus and thereby prevent the supply of respiratory air in the adjoining region—is punctured one or more times with the tip, which is introduced into a working passage of the bronchoscope, of the tubular high-frequency catheter, a high-frequency ac voltage being applied each time. The tissue of the bronchial tumor coagulates. The reduction in volume in the tumor tissue, which is caused by the coagulation effect, should lead in particular to an increase in cross-section with the obstruction to the bronchus being removed.

Treatment Procedure Using the Example of Tumors on the Bile Duct:

A further area of use of an application device with interstitial-endoscopic involvement is the treatment of obstructive tumors in or on the bile duct (ductus choledochus). The individual steps in the treatment are to be carried out with a gastroscope similarly to the treatment of obstructive bronchial tumors. The high-frequency catheter is introduced into the bile duct through a gastroscope (endoscope for the gastrointestinal region) and placed with the distal end in front of the tumor. The tumor which obstructs the bile duct is punctured one or more times with the tip, introduced into a working passage of the gastroscope, of the tubular high-frequency catheter, with a high-frequency ac voltage being applied on each occasion in order to coagulate the tumor tissue. Then at that location a stent (tubular element with which a lumen is safeguarded against obstruction) can be inserted into the bile duct, whereby immediate drainage of the bile fluid is made possible.

Treatment Procedure Using the Example of Gastro-Esophageal Reflux Disease:

Finally the application device with interstitial-endoscopic involvement of the application device is suitable for the treatment of gastro-esophageal reflux disease (GERD). For that purpose the high-frequency catheter of the application device is passed to the stomach entrance (sphincter) by way of an endoscope. The distal end of the endoscope is angled at the level of the sphincter through about 30-90°, the electrode is advanced and caused to penetrate into the sphincter tissue. Thereupon high-frequency current is delivered in order to coagulate the tissue. The healing process induced thereby leads to a constriction of the stomach entrance and reflux of gastric acid into the esophagus is prevented or reduced.

BRIEF DESCRIPTION OF THE DRAWINGS

The invention is described in greater detail hereinafter by means of an embodiment by way of example and with reference to the accompanying drawings in which.

DETAILED DESCRIPTION OF THE DRAWINGS

Figure 1A:
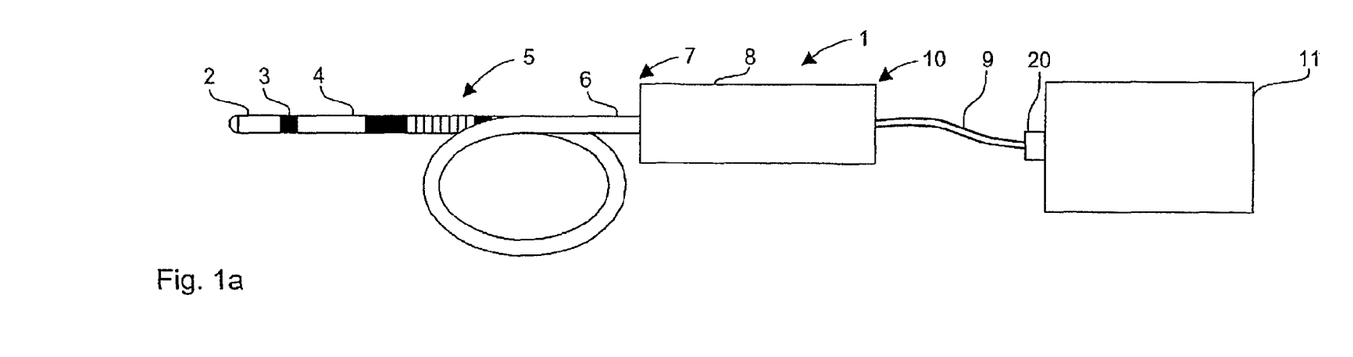
FIGS. 1a and 1b show an application device according to the invention with an enlarged illustration of its distal end.

FIG. 1a shows a flexible application device 1 which is suitable for the high-frequency therapy of biological tissue. The application device 1 includes a connecting element 8, in the interior of which is disposed the electrical and mechanical interface between the cable 9 and the lines within the high-frequency catheter 5.

At its proximal end 10 the connecting element 8 has a through passage, through which a cable 9 is passed. The cable 9 is connected by way of the connection 20 to the supply and control unit 11 with which a high-frequency ac voltage can be generated in per se known manner.

At the distal end 7 of the connecting element 8 a flexible tubular high-frequency catheter 5 is passed through a suitable opening into the interior of the connecting element 8 and fixed there.

The high-frequency catheter 5 includes a shaft tube 6 with a lumen extending therethrough. The casing of the shaft tube 6 is formed from an elastic material, for example a polymer, in particular PEEK.

In addition the high-frequency catheter 5—arranged in succession in the distal direction starting from the connecting element 8—has a proximal electrode 4, an insulator 3 and a head electrode 2 arranged at the distal end of the high-frequency catheter 5.

In the illustrated embodiment the head electrode 2 has a rounded head and is therefore particularly suitable for endoluminal use. For interstitial-endoscopic purposes of use the head electrode 2 can be pointed at its distal end and preferably has a trocar grind or is pointed in a wedge-shaped or conical configuration.

Figure 1B:
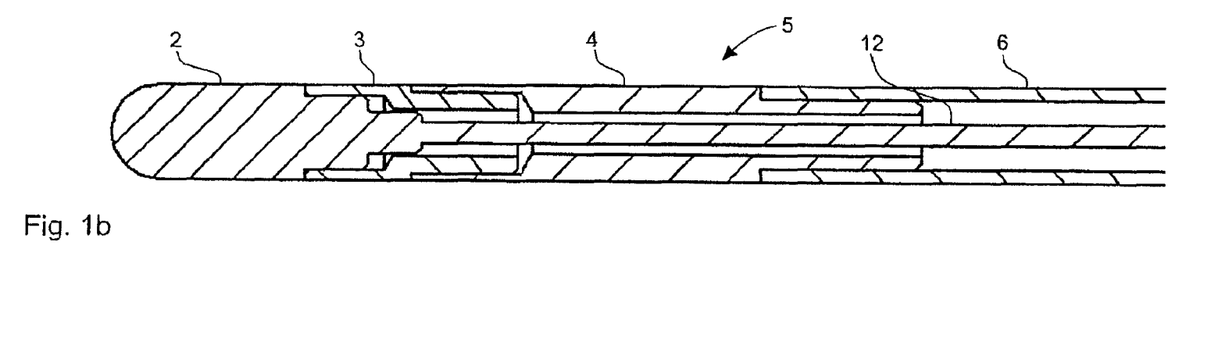

FIG. 1b shows a view on an enlarged scale of the distal end of the application device 1 according to the invention. The traction element 12 for the head electrode 2 is passed centrally through the shaft tube 6 and, being electrically insulated with respect to the proximal electrode 4, goes to the proximal end 13 (see also FIG. 2) of the head electrode 2. The traction element 12 is in the form of a metal wire which preferably comprises stainless V2A steel. To increase flexibility it can be in the form of a braided metal cable. For the purposes of electrical insulation the wire can be partially sheathed with a non-conducting material. The traction element 12 is fixedly connected with its distal end at the proximal end 13 of the head electrode 2, preferably by welding. The head electrode 2 also comprises V2A steel at least in the region of its proximal end 13. The traction element 12 has a tensile strength of at least 1000 N/mm$^2$. In the described embodiment the traction element 12 of the head electrode 2 is of a diameter of 0.4 mm. Proximally, the traction element 12 is mechanically stably connected to the connecting element 8 and electrically conductingly connected to the cable 9 within the connecting element 8.

An electrical feed line (not described in greater detail herein) is passed through the lumen of the shaft tube 6 to the proximal electrode 4. The feed line is electrically conductingly connected to the cable 9 within the connecting element 8. The electrical feed line for the proximal electrode 4 comprises for example copper and is sheathed with an insulator material.

Figure 2:
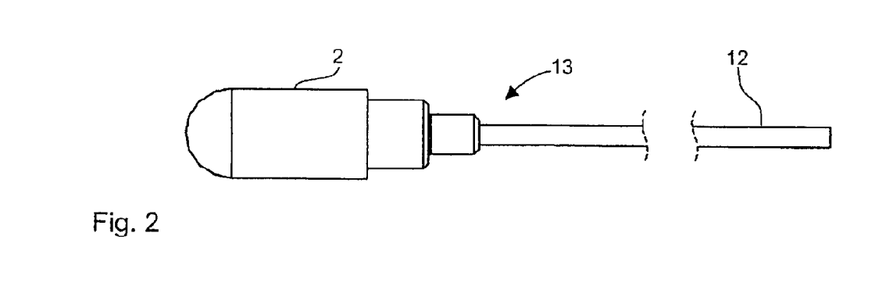
FIG. 2 shows a head electrode with a traction element which at the same time serves as an electrical feed line.

FIG. 2 shows the head electrode 2 with a traction element 12. The traction element 12 is fixedly connected with its distal end at the proximal end 13 of the head electrode 2, preferably by being welded thereto. The head electrode 2 also comprises V2A steel at least in the region of its proximal end 13.

To increase coagulation efficiency the high-frequency catheter 5 can also be provided with an electrode temperature control means. For that purpose in a variant a flushing tube (hollow) is arranged over the traction element 12. In addition, in a variant, the traction element 12 may not be in the form of wire (solid material) but in the form of a tube (hollow). Those variants will be described in greater detail hereinafter with reference to FIGS. 3*a*, 3*b*, FIGS. 4*a* and 4*b*.

Figure 3A:
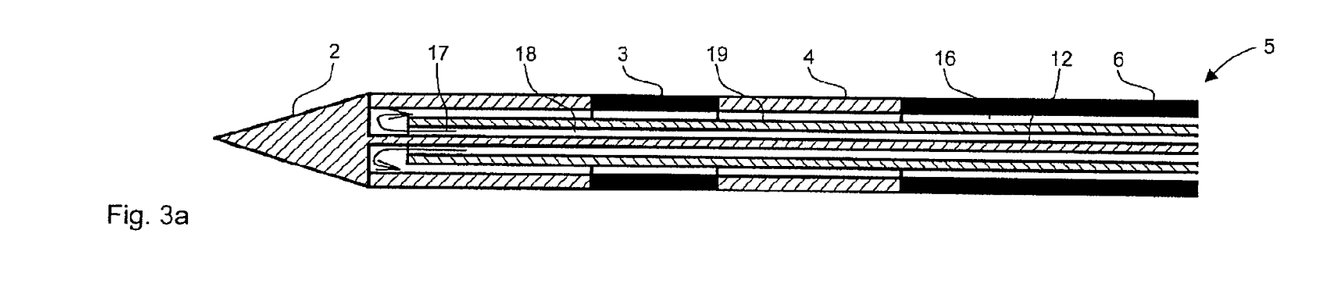
FIGS. 3a and 3b show a diagrammatic view in section by way of example on an enlarged scale of a closed fluid circuit of a variant of the distal end of the application device according to the invention.
Figure 3B:
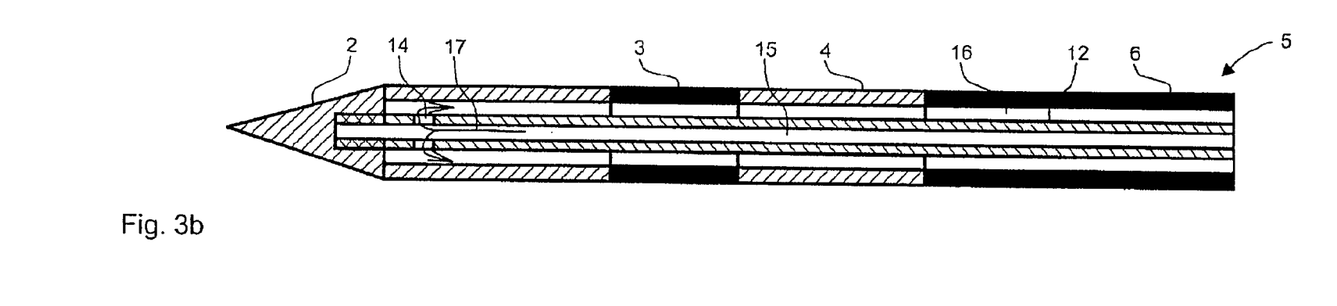

FIGS. 3*a* and 3*b* show a diagrammatic view in section on an enlarged scale by way of example of a closed fluid circuit (counterflow principle) of the distal end of the application device according to the invention.

As shown in FIG. 3*a* a flushing tube 19 is arranged over the traction element 12. Fluid 17 is pumped through the internal lumen 18 of the flushing tube 19 to the distal end of the high-frequency catheter 5, passes through the open distal end of the flushing tube 19 into the space 16 between the flushing tube 19 and the head electrode 2, the insulator 3, the proximal electrode 4, the shaft tube 6 and flows back to the proximal end of the high-frequency catheter 5. The flushing tube 19 preferably comprises a non-conducting flexible material.

FIG. 3*b* shows a variant in which the traction element 12 is not in the form of wire (solid material) but in the form of a tube (hollow). Fluid 17 is pumped through the internal lumen 15 of the traction element 12 to the distal end of the high-frequency catheter 5, passes through the transverse bores 14 into the space 16 between the traction element 12 and the head electrode 2, the insulator 3, the proximal electrode 4 and the shaft tube 6 and flows back to the proximal end of the high-frequency catheter 5. In this variant the traction element 12 preferably comprises a conducting metal alloy such as NiTiNol (alloy consisting of nickel and titanium) or CuAlZn (alloy consisting of copper, aluminum and zinc) or AuCd (alloy consisting of gold and cadmium) or FePt (alloy consisting of iron and platinum).

Figure 4A:
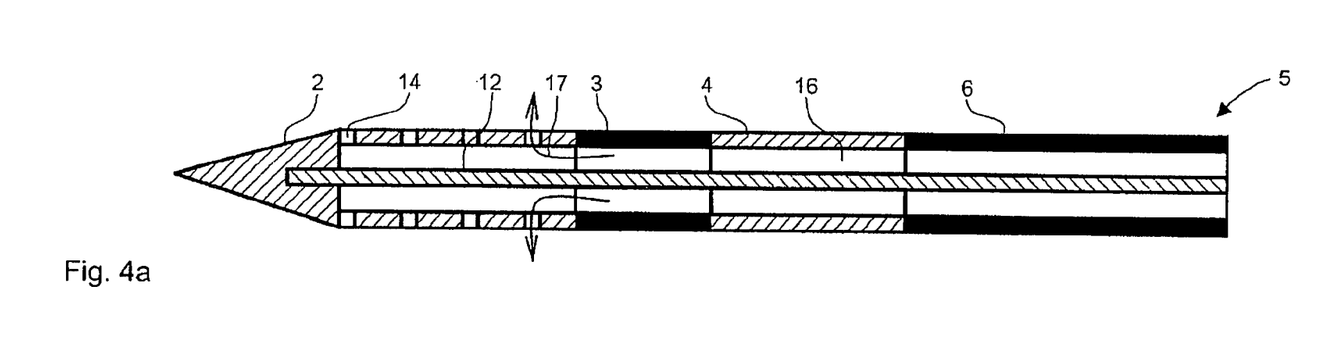
FIGS. 4a and 4b show a diagrammatic view in section by way of example on an enlarged scale of an open fluid flushing arrangement of a variant of the distal end of the application device according to the invention.
Figure 4B:
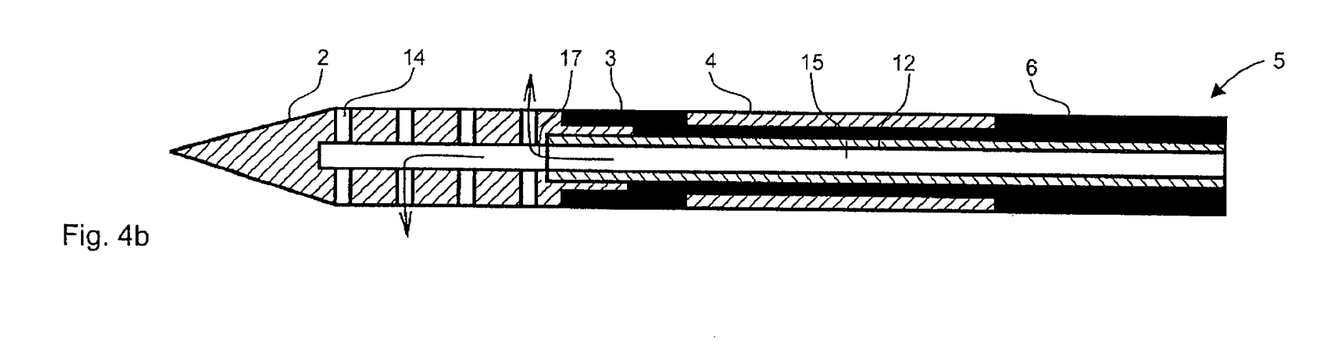

Open flushing can be implemented in the case of high-frequency catheters 5 of small outside diameter. This can be effected in two variants (as shown in FIG. 4*a* and FIG. 4*b*):

FIGS. 4*a* and 4*b* show a diagrammatic view in section on an enlarged scale by way of example of open fluid flushing of a variant of the distal end of the application device according to the invention.

Referring to FIG. 4*a* the traction element 12 to the head electrode 2 is in the form of wire. The fluid 17 is pumped through the space 16 between the traction element 12, the shaft tube 6, the proximal electrode 4, the insulator 3 and the head electrode 2 and issues through bores 14 or slots 14 in the head electrode 2. In a further variant bores 14 or slots 14 can also be provided in the proximal electrode 4.

Referring to FIG. 4*b* the traction element 12 to the head electrode 2 is in the form of a flexible tube. The fluid 17 is pumped through the internal lumen 15 of the traction element 12 to the distal end and issues through bores 14 or slots 14 in the head electrode 2. In this variant the traction element 12 preferably comprises elastic and conducting metal alloys such as NiTiNol (alloy consisting of nickel and titanium) or CuAlZn (alloy consisting of copper, aluminum and zinc) or AuCd (alloy consisting of gold and cadmium) or FePt (alloy consisting of iron and platinum).

The invention claimed is:

1. A flexible application catheter device for high-frequency therapy of biological tissue or hollow organs, the device comprising:
    a flexible shaft tube having a length in an axial direction and comprising at least one lumen inside the flexible shaft tube and having a length in the axial direction, the lumen comprising an inner surface;
    a head electrode arranged at a distal end of the device;
    an electric line with a connection for a high-frequency generator;
    a connecting element between the shaft tube and the electric line; and
    a traction element which extends in the axial direction in the lumen between the head electrode and the connecting element and which is fixedly connected to the head electrode and to the connecting element and which is configured to transmit external mechanical forces which occur during a treatment and which act on the head electrode and to transmit forces transmitted from the flexible shaft tube, to the connecting element,
    wherein a cross-sectional area and a tensile strength of the traction element are configured to transmit external mechanical forces exerted during the treatment acting on the head electrode to the connecting element by way of the traction element; the traction element being sized and positioned so that the traction element is spaced with an empty space in a radial direction transverse to the axial direction from the inner surface of the lumen extending from the head electrode to the connecting element,
    wherein the traction element is electrically conducting and is electrically conductingly connected both to the head electrode and to the connection for the high-frequency generator.

2. An application device as set forth in claim 1, wherein the device comprises an electrically insulating casing which encloses the lumen.

3. An application device as set forth in claim 1, wherein the traction element and a connection to the head electrode is of a tensile strength in a range of between 70 and 300 N/mm.

4. An application device as set forth in claim 1, wherein the traction element comprises entirely or in parts stainless steel or a conducting metal alloy.

5. An application device as set forth in claim 1, wherein the traction element is an internally hollow tube.

6. An application device as set forth in claim 5, wherein characterised in that provided at the distal end of the device is at least one opening which leads outwardly from the internal lumen of the traction element and guides fluid to the at least one opening so as to allow the fluid to issue at the at least one opening.

7. An application device as set forth in claim 6, wherein the openings are bores or slots in the proximal electrode.

8. A method of operating an application device as set forth in claim 7, comprising passing an electrically conducting fluid through the hollow tube.

9. A method of operating an application device as set forth in claim 7, comprising passing a therapeutically effective medicament as the fluid through the hollow tube.

10. A method of operating an application device as set forth in claim 7, comprising passing a toxic substance as the fluid through the hollow tube.

11. A method of operating an application device as set forth in claim 7, comprising passing a mixture of electrically conducting, therapeutically effective and toxic substances as the fluid through the hollow tube.

12. An application device as set forth in claim 5, wherein the traction element is an internally hollow tube which comprises a fluid-tight plastic material which is sheathed by an electrically conducting wire mesh or into which an electrically conducting wire mesh is incorporated.

13. An application device as set forth in claim 12, wherein the head electrode comprises stainless steel or a conducting metal alloy at least in a connecting region of the traction element.

14. An application device as set forth in claim 5, wherein an internal lumen of the traction element and a hollow space of the high-frequency catheter, that extends along the traction element, are in fluid communication with each other in a region of the distal end of the high-frequency catheter and form a closed fluid guide system (counterflow principle).

15. An application device as set forth in claim 14, wherein the internal lumen of the traction element is provided in the distal region with at least one transverse bore through which liquid can pass into a hollow space between the traction element and a shaft tube and can flow back to a proximal end of the high-frequency catheter.

16. An application device as set forth in claim 1, wherein the traction element has a fixed diameter sized in a range of between 0.2 and 0.8 mm, in particular being about 0.4 mm.

17. An application device as set forth in claim 1, wherein the traction element is a wire.

18. An application device as set forth in claim 17, wherein the traction element is a braided wire which has a large number of individual filaments.

19. An application device as set forth in claim 1, wherein the shaft tube is of an outside diameter which approximately corresponds to the outside diameter of the head electrode at a proximal end thereof.

20. An application device as set forth in claim 19, wherein the device comprises a proximal electrode electrically insulated with respect to the head electrode and which is arranged in the proximity of the distal end of the device in proximal relationship with the head electrode and is electrically conductingly connected by way of a second electrically conducting feed line to a second contact location in the connecting element.

21. An application device as set forth in claim 20, wherein a spacing of the proximal electrode from the head electrode in the axial direction of the is between 5 and 20% of the overall electrode length.

22. An application device as set forth in claim 21, wherein the shaft tube is of an outside diameter which approximately corresponds to an outside diameter of the proximal electrode and a largest diameter of the head electrode.

23. An application device as set forth in claim 22, wherein the outside diameter is less than or equal to 3.5 mm.

24. An application device as set forth in claim 23, wherein the length of the shaft tube is between 300 and 3000 mm.

25. An application device as set forth in claim 24, wherein a length of the traction element is between 300 and 3000 mm.

26. An application device as set forth in claim 25, wherein an outside diameter of the head electrode at a proximal end thereof is a largest diameter of the head electrode.

27. An application device as set forth in claim 26, wherein the application device is designed for endoluminal or interstitial-endoscopic use.

28. An application device as set forth in claim 27, wherein the head electrode at the distal end is shaped in the manner of a trocar tip.

29. An application device as set forth in claim 27, wherein the head electrode at the distal end is hemispherical.

30. An application device as set forth in claim 27, wherein the head electrode at the distal end terminates in a conical configuration.

31. An application device as set forth in claim 30, wherein a non-conducting flexible flushing tube is arranged over the traction element and a hollow space of the device, that extends along the flushing tube, are in fluid communication with each other in the region of the distal end of the device and form a closed fluid guide system.

32. An application device as set forth in claim 31, wherein the internal lumen of a flushing tube in a distal region has an opening configured to conduct fluid into the hollow space between the traction element and a shaft tube and can flow back to a proximal end of the device.

33. An application device as set forth in claim 30, wherein provided at a distal end of the device is at least one opening which leads outwardly from a hollow space extending from a proximal end of the shaft tube to the at least one opening between the traction element and the shaft tube and guides fluid through the hollow space to the at least one opening so as to allow the fluid to issue at the at least one opening.

* * * * *

UNITED STATES PATENT AND TRADEMARK OFFICE
CERTIFICATE OF CORRECTION

PATENT NO. : 8,452,422 B2  Page 1 of 1
APPLICATION NO. : 11/920400
DATED : May 28, 2013
INVENTOR(S) : Desinger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 972 days.

Signed and Sealed this
Eighth Day of September, 2015

Michelle K. Lee
*Director of the United States Patent and Trademark Office*